(12) United States Patent
Kuzelka

(10) Patent No.: US 10,117,959 B2
(45) Date of Patent: Nov. 6, 2018

(54) SMART STERILIZATION TRACKER TAG

(71) Applicant: General Electric Company, Schenectady, NY (US)

(72) Inventor: Russell James Kuzelka, Madison, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/175,561

(22) Filed: Jun. 7, 2016

(65) Prior Publication Data

US 2017/0348452 A1    Dec. 7, 2017

(51) Int. Cl.
| | |
|---|---|
| G08B 13/14 | (2006.01) |
| A61L 2/28 | (2006.01) |
| A61L 2/07 | (2006.01) |
| G06K 7/10 | (2006.01) |
| A61L 2/26 | (2006.01) |
| A61B 90/90 | (2016.01) |

(52) U.S. Cl.
CPC ............... *A61L 2/28* (2013.01); *A61B 90/90* (2016.02); *A61L 2/07* (2013.01); *A61L 2/26* (2013.01); *G06K 7/10366* (2013.01); *A61L 2202/14* (2013.01); *A61L 2202/24* (2013.01)

(58) Field of Classification Search
CPC ............. G06K 7/10; A61L 2/00; A61M 1/168
USPC ........ 340/572.1–572.9, 539.12, 573.1, 12.51
See application file for complete search history.

(56) References Cited

U.S. PATENT DOCUMENTS

| | | |
|---|---|---|
| 7,312,752 B2 | 12/2007 | Smith et al. |
| 7,324,824 B2 | 1/2008 | Smith et al. |
| 7,443,297 B1 | 10/2008 | Baranowski et al. |
| 7,504,928 B2 | 3/2009 | Nierenberg et al. |
| 7,636,046 B2 | 12/2009 | Caliri et al. |

(Continued)

FOREIGN PATENT DOCUMENTS

| | | |
|---|---|---|
| WO | 2008061313 A1 | 5/2008 |
| WO | 2014071337 A1 | 5/2014 |
| WO | 2014165620 A1 | 10/2014 |

OTHER PUBLICATIONS

International Search Report and Written Opinion for PCT/US2017/035977, dated Aug. 3, 2017, 12 pages.

*Primary Examiner* — Phung Nguyen
(74) *Attorney, Agent, or Firm* — Boyle Fredrickson, S.C.

(57) ABSTRACT

In the present invention, a device, system and associated method is provided, as a compact, automated and self-contained data logger with capability of withstanding conditions used in sterilizing reusable medical device equipment/components. The device includes one or more sensors to automatically sense and store information on the parameters of various autoclave cycle(s) for the component associated with the tracking device and their respective timestamps of each autoclave cycle(s). This information is stored in a data record on the tracking device for the individual component. The data record can be used as evidence of valid sterilization cycles for the component and can also provide information for the host system and/or the user of the status for the component, including the last time the component was sterilized, the time between sterilization cycles, the time for replacement of the component, and too warn if the device was returned to service without proper sterilization.

19 Claims, 3 Drawing Sheets

(56) References Cited

U.S. PATENT DOCUMENTS

| | | | |
|---|---|---|---|
| 7,701,334 B1* | 4/2010 | Perkins | G06F 19/327 |
| | | | 340/539.13 |
| 7,941,096 B2 | 5/2011 | Perkins et al. | |
| 8,040,238 B2 | 10/2011 | Perkins | |
| 8,600,374 B1 | 12/2013 | Hertlein et al. | |
| 9,107,690 B2* | 8/2015 | Bales, Jr. | A61B 17/320092 |
| 2006/0176179 A1* | 8/2006 | Skorpik | G06K 19/0717 |
| | | | 340/572.8 |
| 2007/0284428 A1 | 12/2007 | Cambre et al. | |
| 2008/0012767 A1 | 1/2008 | Caliri et al. | |
| 2008/0252459 A1* | 10/2008 | Butler | G06K 7/0008 |
| | | | 340/572.1 |
| 2011/0163850 A1* | 7/2011 | Bachman | G06K 19/0702 |
| | | | 340/10.1 |
| 2015/0374868 A1* | 12/2015 | Bruce | A61L 2/208 |
| | | | 422/3 |
| 2015/0379838 A1* | 12/2015 | Xie | G08B 13/242 |
| | | | 340/572.3 |

* cited by examiner

SMART STERILIZATION TRACKER TAG

BACKGROUND OF INVENTION

The subject matter disclosed herein relates to the field of re-usable medical equipment or components and sterilization methods therefore, and more specifically to devices and methods for determining the sterilization status and useful life of these types of re-usable equipment and components.

To assist in in the performance of different medical procedures a number of replaceable equipment and components for different medical devices for use in these procedures have been developed. These components can be used in a procedure for a particular patient and then sterilized for use in another procedure on the, same or a different patient. After the component has been put through a number of sterilization cycles and thus reached the end of its useful life, then the component can be disposed of and replaced with an identical component, increasing the ease of performance of the procedures utilizing the component.

One of the significant issues with re-usable components of this type concerns the sterilization of the components between subsequent uses. In particular, ensuring that the components/equipment moving from patient to patient have gone through appropriate sterilization/decontamination is a significant issue for the Joint Commission on Accreditation of Healthcare Organizations (JCAHO) in regard to infection controls Healthcare-associated infections (HAI) are most commonly caused by viral, bacterial, and fungal pathogens. Patient-related risk factors for invasion of colonizing pathogen include severity of illness, underlying immunocompromised state and/or the length of in-patient stay. Most patients who have healthcare-associated infections caused by bacterial and fungal pathogens have a predisposition to infection caused by invasive supportive measures, equipment and components, e.g., such as endotracheal intubation, placement of intravascular lines, urinary catheters, etc.

To illustrate the importance of proper sterilization/decontamination of these types of components/equipment, in the United States healthcare-associated infections (HAI) are estimated to occur in 5% of all hospitalizations. Internationally, both developed and resource-poor countries are fitted with the burden of healthcare-associated infections. In a World Health Organization (WHO) cooperative study, about 8.7% of hospitalized patients had developed nosocomial infections. A 6-year study from 2002-2007 involving intensive care units (ICUs) in Latin America, Asia, Africa, and Europe, using the Center for Disease Controls definitions, revealed higher rates of Ventilator Associated Pneumonias (VAP) than those of comparable United States ICUs. In March 2009, the CDC released a report, estimating overall annual direct medical costs of healthcare-associated infections that ranged from $28-45 billion. Among pediatric patients, children younger than 1 year, babies with extremely low birth weight (1000 g) and children in either the PICU or NICE have higher rates of healthcare-associated infections. For example, of the hospital acquired infections recently studied among pediatric intensive care units. 95% of all pneumonia cases were in patients undergoing mechanical ventilation.

Most medical devices/components are typically reprocessed/sterilized on a periodic basis that can vary depending on the infection control policy for the particular institution. In addition, the cleaning and autoclave schedule can vary by institution, region or availability of autoclave facilities. However, infections from inadequately reprocessed/sterilized devices are not often recognized and the number of HAIs that can be attributed to inadequate device reprocessing is unknown because it is not, often investigated as a cause of HAI.

To attempt to address the issue certain prior art devices have been developed that assist in the sterilization of these components to limit the occurrences of HAIs. In one prior art example, disclosed in U.S. Pat. No. 8,600,374 entitled Sterilizable Wireless Tracking And Communication Device And Method For Manufacturing, which is expressly incorporated herein by reference for all purposes, a wireless communication device is provided that includes a circuit board within a water-tight enclosure. The device includes sensors capable of sensing and monitoring the environment in which the device is positioned, such as a motion sensor, a temperature sensor and/or a pressure sensor. When these sensors detect a change in the environment of the device, such as when the device is positioned within an autoclave, that information is wirelessly transmitted to a network. The sensors, also send a signal to the network when the change to the environment of the device is removed, such as when the device is removed from within the autoclave. The information transmitted by the device to the network can include in addition to the signal representative of the chance in the environment of the device, the time the changes occurred, the value of the changes, and the position of the device. This information can then be compared with standards for the sterilization of the device and any medical equipment or components associated with the device, in order to determine whether the equipment/components have been sufficiently sterilized.

However, while providing useful information about the level of sterilization applied to the equipment or component in a particular sterilization cycle, the prior art concerns only the sterilization of the equipment or component and does not address other issues concerning the ongoing utility of the particular component, which must be assessed visually or in some other non-standardized manner.

Hence it is desirable to provide a device and method for qualification of valid autoclave cycle, but that also integrates the data obtained by the device into the system or network for further use/processing by the network to provide additional information on the particular component, such as predictive end-of-life calculations, intelligent service metrics, and institutional infection control compliance, among others.

BRIEF DESCRIPTION OF THE INVENTION

There is a need or desire for a device, system and method that can improve clinical management of medical accessory/equipment/component reprocessing to result in improvement of patient clinical outcome due to reduced risk of Hospital Acquired Infection (HAI) and cross contamination at the host device level.

A medical device is provided that includes a higher level of automated intelligence in order to more effectively utilize data recorded by the device concerning the sterilization of a re-processable medical accessory/component.

In an exemplary embodiment of the device and associated method, a tracking device including high operating-temperature electronics and an autoclavable power source is provided as a compact, automated and self-contained simple data logger with capability of withstanding the high ambient temperature and extreme steam heat used in sterilizing reusable medical device equipment/components. The device includes one or more sensors to automatically sense and store information on the parameters of various autoclave cycle(s) for the component associated with the tracking device, such as the starting and ending temperatures and their respective timestamps of each autoclave cycle(s). This information is stored within in a data record on the tracking device for the individual equipment/component. The data record stored on the tracking tag for the component can be used as objective evidence of valid autoclave sterilization cycles for the component. The stored data can also provide information for the host system and/or the user of the status for the component, including information related to the last time the component was sterilized, the time between sterilization cycles, the time for replacement of the component, and to provide a warning if the device was returned to service without proper sterilization, among other types of information.

According to one exemplary embodiment of the invention, a tracking tag is provided that includes a sterilization-resistant housing, a microprocessor, at least one sensor connected to the microprocessor and configured to sense a sterilization parameter regarding the sterilization of the component, an electronic storage unit connected to the microprocessor and configured to record, data from the sensor on the sterilization status of the component, and a wired/wireless network interface operably connected to the microprocessor.

According to one exemplary embodiment of the invention, a system for sensing and recording information concerning a sterilization status of a component of a medical device, includes a sterilizable component, a tracking tag secured to the component, the tag including a sterilization-resistant housing containing a microprocessor, a sensor connected to the microprocessor and configured to, sense a sterilization parameter regarding the sterilization of the component, and an electronic storage unit connected to the microprocessor and configured to record data from the sensor on the sterilization status of the component, and a medical device connectable to the component, the device including a central processing unit able to receive data stored on the tag regarding the sterilization status of the component According to another exemplary embodiment of the invention, a method of tracking the sterilization of a sterilizable component for a medical device includes providing a tracking tag including a sterilization-resistant housing containing a microprocessor, a sensor connected to the microprocessor and configured to sense a sterilization parameter regarding the sterilization of the component, and an electronic storage unit connected to the microprocessor and configured to record data from the sensor on the sterilization status of the component securing the tag to the component sterilizing the component and the tag, and recording data concerning the sterilization status of the component within the tag.

It should be understood that the brief description above is provided to introduce in simplified form a selection of concepts that are further described in the detailed description. It is not meant to identify key or essential features of the claimed subject, matter, the scope of which is defined uniquely by the claims that follow the detailed description. Furthermore, the claimed subject matter is not limited to implementations that solve, any disadvantages noted above or in any part of this disclosure

DESCRIPTION OF THE DRAWINGS

The drawings illustrate the best mode presently contemplated of carrying out the disclosure. In the drawings.

DETAILED DESCRIPTION OF THE DRAWINGS

In the following detailed description, reference is made to the accompanying drawings that form a part hereof, and in which is, shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
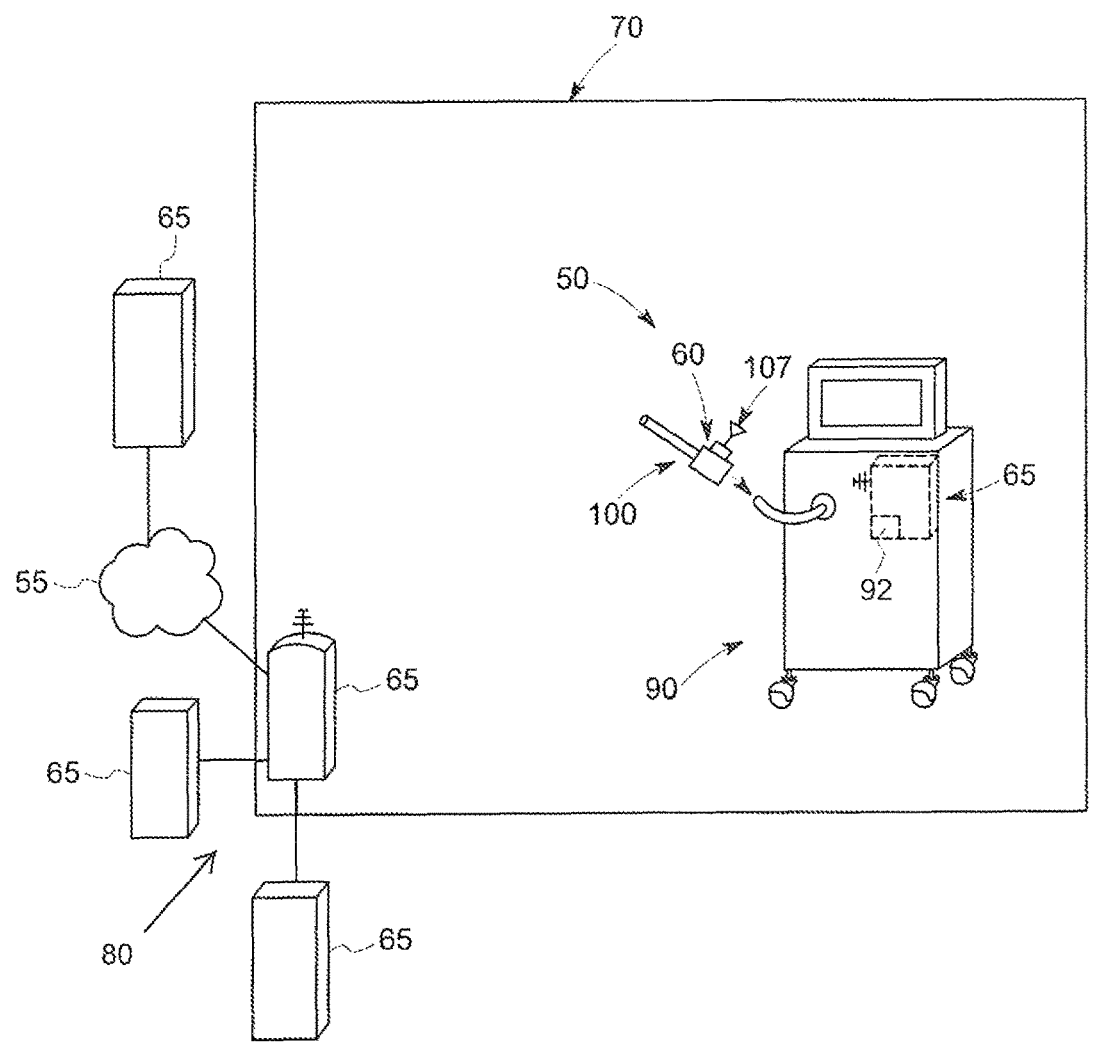
FIG. 1 is a schematic view of a sterilization tracking tag system according to an exemplary embodiment of the invention.

Exemplary embodiments of the invention disclosed herein relate to a tracking device or tag, associated system and method of use for tracking a component of a medical device associated with the tag as it moves through different sterilization cycles during the useful life of the component, With this in mind, one exemplary embodiment of a wireless asset tracking system such as that disclosed in U.S. Pat. No. 8,600,374, entitled Sterilizable Wireless Tracking And Communication Device And Method For Manufacturing, which is expressly incorporated herein by reference for all purposes, is generally designated 50 in FIG. 1. The system 50 is capable of determining of tracking the sterilization of a component 100 within a facility 70. The system 50 can be configured to include a plurality of tags 60 and at least one central processing unit or server 65, which can be incorporated into a general computer network 80 for the facility 70, or which can be a part of a medical device 90 with which the component 100 is utilized, which can also be connected to the network 80. Examples of the components of the system 50 are disclosed in Smith et al., U.S. Pat. No. 7,312,752 for a Wireless Position Location And Tracking System, which is hereby incorporated by reference in its entirety for all purposes and in Smith et al. U.S. Pat. No. 7,324,824 for a Plug-In Network Appliance, which is also hereby incorporated by reference in its entirety for all purposes.

The system 50 is employed within a facility 70 such as a hospital, healthcare facility, or other like facility. The system 50 is utilized to track and obtain sterilization information on various sterilizable objects/components 100 associated with the tags 60 positioned throughout the facility 70. The tags 60 are secured to the objects or components 100 in any suitable manner such that the tags 60 remain attached to the components 100 as the components 100 move through the facility 70 and through sterilization cycles performed on the components 100 within the facility 70. In a hospital setting, the sterilizable objects 100 could include surgical equipment, nursing equipment and the like. Sterilization is generally defined as a process which achieves the complete killing of all microorganisms, especially bacterial spores. As used herein, sterilization is defined in a broader sense to include cleaning, disinfecting and/or sterilizing.

The tags 60 can be configured transmit signals to the server 65 in a known wired or wireless manner. In an exemplary embodiment of a wired connection, the tags 60 can be physically connected via an electrical connector (not shown) on the tag 60 to a suitable docking station (not shown) that is connected to the server 65 via wired connection (not shown). Data collected by and stored on the tag 60 can then be directly transmitted from the tag 60 through the wired connection to the server 65.

In another exemplary embodiment, referring again to FIG. 1, the tags 60 can wirelessly communicate to the server 65. The tags 60 transmit signals which are received by the server 65 via a suitable wireless receiver (not shown) operably connected to the server 65. The server 65 is preferably located on-site at the facility 70, such as in the medical device 90. However, the system 50 may also include one or more off-site servers 65, connected via the Internet 55.

In one exemplary embodiment, each tag 60, or wireless communication device, preferably transmits a radio frequency signal. Each device 60 may use a low-power, medium range (1 foot to 30 feet) wireless communication system. Such wireless communication systems include ZIG-BEE, BLUETOOTH, Low-Power BLUETOOTH, WiFi or Low-Power WiFi, UltraWide Band ("UWB"), Ultrasound and Infrared communication systems. A preferred radio-frequency signal is approximately 2.48 GigaHertz ("GHz"). The communication format is preferably IEEE Standard 802.15.4. Those skilled in the pertinent art will recognize that the tags 60 may operate at various frequencies without departing from the scope and spirit of the present invention. The tags 60 may be constructed with an asset theft protection system such as disclosed in Baranowski et al., U.S. Pat. No. 7,443,297 for a Wireless Tracking System And Method With Optical Tag Removal Detection, which is hereby incorporated by reference in its entirety for all purposes. The tags 60 and near-field communication devices may be designed to avoid multipath errors such as disclosed in Nierenberg et al., U.S. Pat. No. 7,504,928 for a Wireless Tracking System And Method Utilizing Tags With Variable Power Level Transmissions, and Calliri et al., U.S. Patent Publication Number 2008/0012767 for a Wireless Tracking System And Method With Multipath Error Mitigation, both of which are hereby incorporated by reference in their entireties for all purposes.

A description of sterilizable tags 60 and systems using sterilizable tags is found in Caliri et al., U.S. Pat. No. 7,636,046 for Wireless Tracking System And Method With Extreme Temperature Resistant Taw, which is hereby incorporated by reference in its entirety for all purposes. Another description of a sterilizable tag 60 and systems using sterilizable tags is found in Perkins et al., U.S. Pat. No. 7,701,334 for Wireless Tracking System And Method For Sterilizable Object, which is hereby incorporated by reference in its entirety for all purposes. In another embodiment, the tags 60, or wireless communication devices, are used with or as near-field communication devices such as disclosed in Perkins, U.S. Pat. No. 7,941,096 for Wireless Tracking System And Method Utilizing Near-Field Communication Devices, which is hereby incorporated by reference in its entirety for all purposes. In another embodiment the tags 60, or wireless communication devices, are used with or as back-hauling communication devices such as disclosed in Perkins, U.S. Pat. No. 8,040,238 for Wireless Tracking System And Method For Backhaul Of Information, which is hereby incorporated by reference in its entirety for all purposes.

Figure 2:
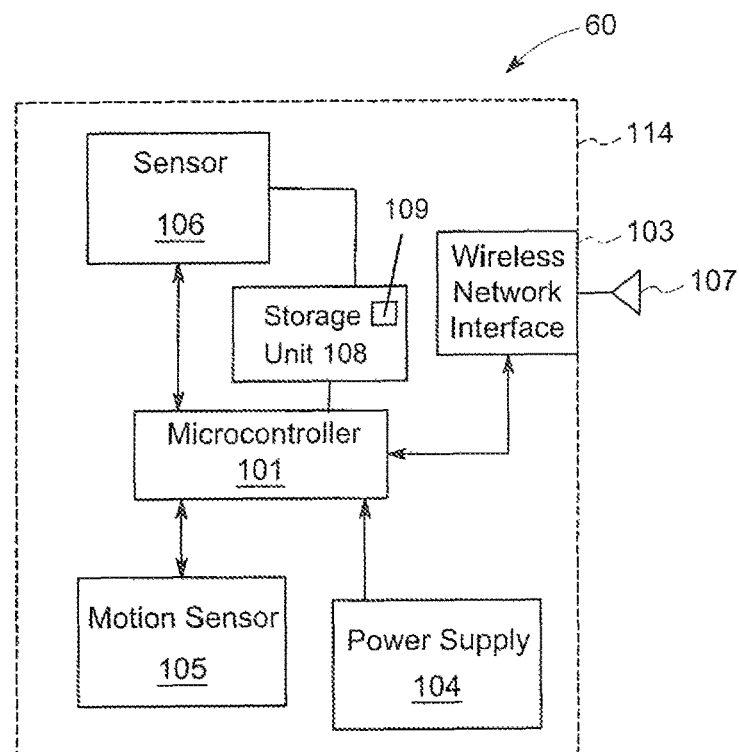
FIG. 2 is a schematic view of a sterilization tracking tag according to a first exemplary embodiment of the invention.

As shown in FIG. 2, in an exemplary embodiment the tag 60, or wireless communication device, is a self-contained device that includes a microcontroller or processor 101 with an associated electronic storage unit or memory 108, a wireless network interface 103 having an antenna 107, a power supply 104, a motion sensor 105 and a sensor 106. The processor 101 is in communication with the sensor 106, motion sensor 105 and wireless network interface 103. The power supply 109 provides power to the processor 101, the motion sensor 105, the sensor 106 and the wireless network interface 103. The power supply 104 in one exemplary embodiment is a battery, such as a thin and flexible or coin cell sized primary battery, with a design life of at least one hundred (100) steam-autoclave cycles and a five (5) year battery life. Conserving the energy use of the tag 60 allows the tag 60 to have greater use period before needing to be recharged or replaced. In alternative embodiments, the power to the tag 60 could be provided via a wireless charging mechanism within the tag 60 and a wireless (inductive) power transmission mat (not shown) on which the component 100 incorporating the device 60 is placed within the autoclave chamber. In still an alternative embodiment, a rechargeable, high temperature super capacitor could also be used as the power supply 104.

Figure 3:
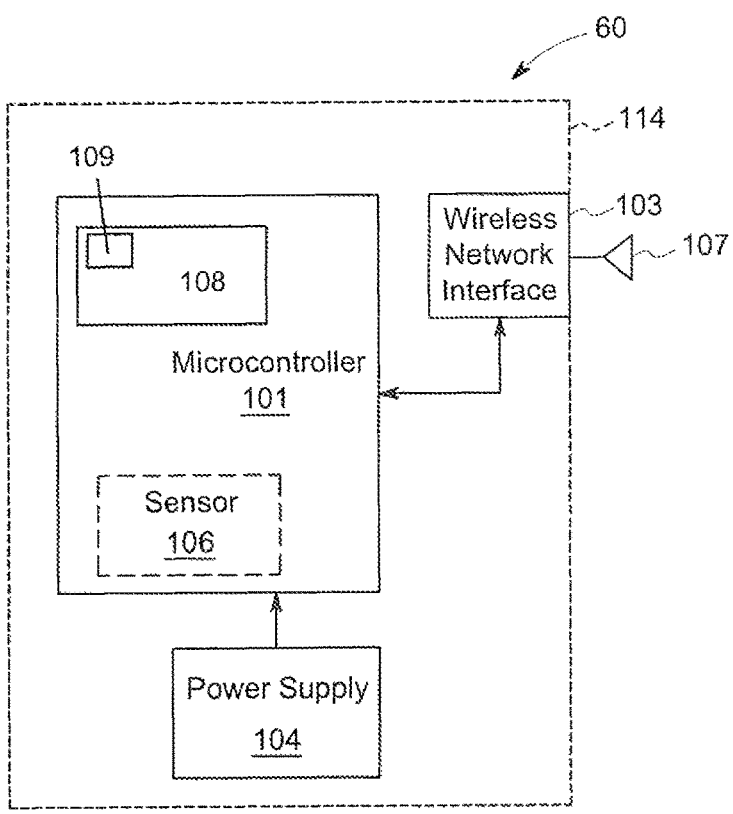
FIG. 3 is a schematic view of a sterilization tracking tag according to a second exemplary embodiment of the invention.

In one embodiment, the sensor 106 can be a separate component from the microcontroller 101 (FIG. 2) or can be integrated into the microcontroller 101 (FIG. 3) in a known manner. The sensor 106 can record one or more of the temperature and/or additional environmental variables such as shock, pressure, or humidity, among other parameters, if required based on the specified application environment for the tag 60. The operational settings of the sensor 106 for the detection of one or more of these parameters can additionally be programmed into the device 60 by the end user in order to more specifically customize the tag 60 for the particular application.

The components of the tag 60 are enclosed within a housing 114. In an exemplary embodiment, the housing 114 is composed of an extreme temperature resistant and moisture resistant material. The electrical components of the tag 60 are contained within the housing 114, and the housing 114 is welded or otherwise closed in manner, such as by ultrasonic welding, to prevent the entry of moisture, dirt or other contaminants into the housing 114. Those skilled in the pertinent art will recognize that the dimensions of the housing 114 may be adapted to a tag 60 for various sterilizable objects/components 100 without departing from the scope and spirit of the present invention.

Figure 4:
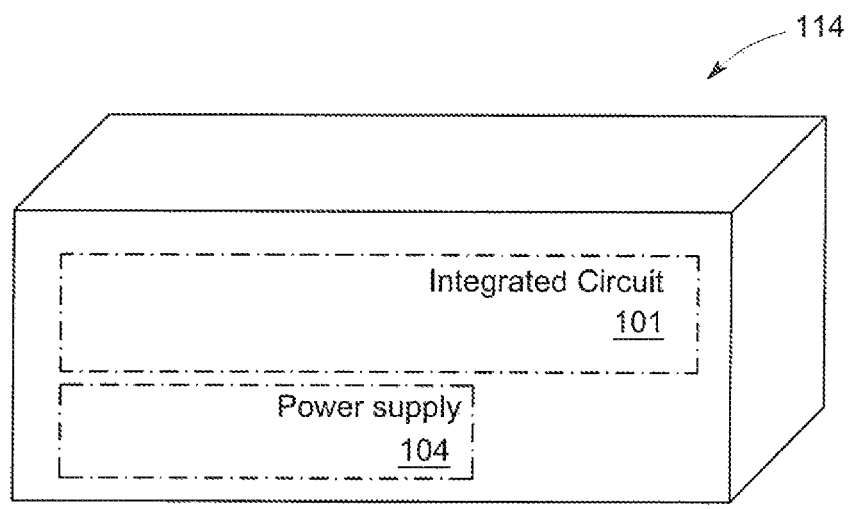
FIG. 4 is a schematic view of a sterilization tracking tag according to a third exemplary embodiment of the invention.

As shown in FIG. 4, in an alternative exemplary embodiment the tag 60 has a housing 114 with an integrated circuit 101 and power supply 104 therein. The electrical components of the tag 60, such as the microcontroller or processor, memory, a wireless network interface having an antenna, a sensor, and an analog-to-digital converter, are located on the single integrated circuit 101 which are available from various commercial sources, such as Texas Instruments. Those skilled in the pertinent art will recognize that other exemplary integrated circuits 101 may be used without departing from the scope and spirit of the present invention.

In any embodiment, the tag 60 is secured to the component 100 in a manner suitable to maintain the tag 60 on the component during the sterilization cycle and during use of the component 100 after each cycle. For example, the tag 60 can be secured to the component 100 by a suitable adhesive (in the form of a battery-assisted smart label), welding, a suitable mechanical fastening member or mechanism, or by integrating the tag 60 directly into the construction of the component 100.

Figure 5:
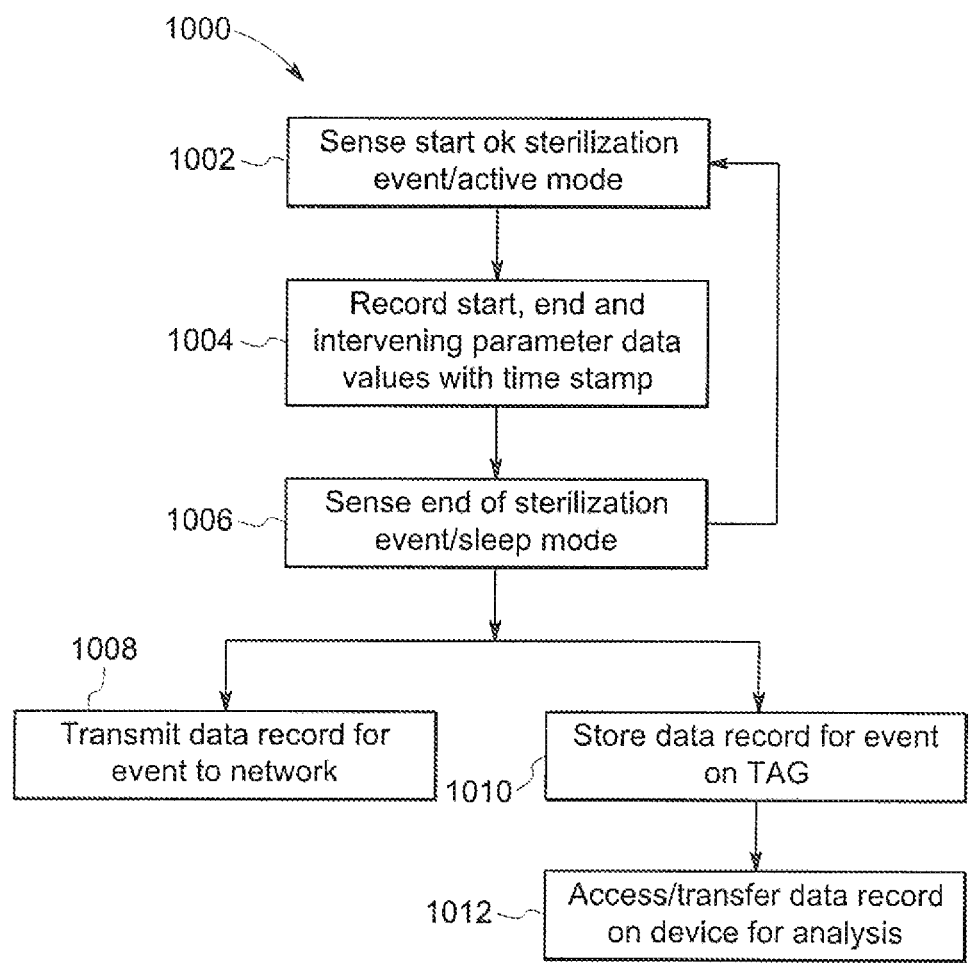
FIG. 5 is a flowchart of a method of operation of sterilization tracking tag system according to an exemplary embodiment of the invention.

An exemplary method 1000 for real-time location monitoring of a sterilizable component 100 is illustrated in FIG. 5. At block 1001, a sterilizable object 100 having a tag 60, or wireless communication device, is tracked in the facility 70. In this exemplary embodiment, the tag 60 can be integrated/adapted to emit signals in a known manner for reception by a Real Time Location System (RTLS) (not shown) already deployed in the facility as part of an enterprise asset management solution in order to located the tag 60, and thus the associated component 100 within the facility 70. If the facility 70 is properly equipped, wireless or RFID communications between the tag 60 and the network 50 can be used to provide fully automated, real-time 24 hour monitoring and reporting capabilities in compliance with an existing facility Real. Time Location System (RTLS).

When the sterilizable object 100 is subjected to a sterilization cycle, such as in an autoclave, at block 1002 the tag 60 can automatically wake from a low-power sleep mode upon sensing the external thermal event trigger via the sensor 106, or other parameter event trigger if the sensor 106 is configured to detect other parameters for the sterilization process. In block 1004, the tag 60 proceeds to record the timestamp, such as via an internal real time clock on the microprocessor 101 in a known manner, and temperature and/or other parameters of both the start and end of the thermal event/sterilization cycle and at a defined number of sample points in between to form a data record 109 for the sterilization status of the component 100 in internal memory 108 on the microprocessor 101. In block 1006 the tag 60 returns to sleep mode when the thermal cycle is complete until the next sterilization event/cycle is sensed and the tag activate again in block 1002. The start and end temperatures for the sterilization cycle that are detected by the tag 60 and cause the tag 60 to begin and stop recording data on the sensed temperature can be user-defined to establish the qualified entry and exit parameter, e.g., temperature, criteria or values for a particular, validated autoclave cycle to which the tag 60 and associated component 100 were subjected, and which can also be contained in the data record 109.

Once the sterilization cycle is completed, in one exemplary embodiment, in block 1008 the tag 60 transmits the recorded data to a server 65 on the network 80. The data is stored in a data record on the network 80 for the component 100 which can be accessed for on-demand interrogation by biomed, field service or reprocessing personnel, as well as to report out the systems most-recent reprocessing status to a hospital Integrated Healthcare Delivery Network (IHDN).

Alternatively, or in conjunction with the transmission of the data to the network 80, in block 1010 the tag 60 retains the data record 109 on the sterilization status of the component 100 in memory 108 for interrogation by or transfer of a copy of the data record 109 to a medical device 90 with which the component 100 is utilized. The device 90 uses a wired or wireless (i.e., near field communication) to obtain the data record 109 from the memory 108 within the tag 60 on the component 100 for review and/or inclusion in the service history data 92 relating to and stored within the server 65/host system/medical device 90. This builds additional intelligence into the host system/medical device 90 that can be accessed for analysis of the data record 109 by a user in block 1012, including the ability for: 1) predicting component end-of-life (EOL) e.g., EOL can be based on the predicted reliability after a defined number of autoclave cycles or the original equipment manufacturers maximum number of allowed autoclave cycles; 2) providing relevant autoclave history (time and date stamps) from the data record 109 for the component 100 to equipment technicians servicing the host system/medical device 90; 3) improving host system/medical device 90 compliance to hospital infection control policy, i.e., in terms of sterilization/autoclave frequency for institutional risk assessment and control/auditing. This data in the data record 109 concerning the sterilization status of the component 100, i.e., the last time sterilized, time between sterilization cycles, time for replacement of the component 100, if the component 100 was returned to service without proper sterilization, etc., can also be integrated into the active alarm/notification management system (not shown) of the host system/medical device 90 for operation of the host system/medical device 90. In an exemplary embodiment, the sterilization history/data record 109 stored in memory 108 in the tag 60 for the component 100 can additionally be used in a proactive method to provide an informational alert to the user via the host system/medical device 90 when, the component 100 should next be sterilized, based on time/cycle/patient parameters defined by the user.

In addition, information or data from the network 80 and/or device 90 can be written to the memory 108 and/or data record 109 on the tag 60, such as alterations to the sterilization parameters stored in memory 108 or regarding the use of the component 100 with the device 90, such that the information from the network 80/device 90 would be contained on the tag 60.

In an exemplary embodiment, the tag 60 can be secured or incorporated within an autoclavable anesthesia flow sensor 100 to be used, with an anesthesia system 90. When brought into the vicinity of (via wireless or near field communications) or connected to (via wired communication) the anesthesia system 90 after sterilization and recordal of the sterilization cycle in the data record 109, the system 90 can interrogate the tag 60 on the flow sensor 100 via a proprietary/secure communication scheme in order to actively relay this information, i.e., the data record 109, back to the system 90 for inclusion in the device service history record 92. In this manner, the tag 60 and system 50 provides an automated manner in which to monitor, record and track the quality/effectivity of the sterilization status of a medical component 100, such that sterilization compliance can be more easily and completely documented as part of the operational log for the medical device 90 utilizing the component 100.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system for sensing and recording information concerning a sterilization status of a component of a medical device, the system comprising:
   a sterilizable component;
   a tracking tag secured to the component, the tag including
      a sterilization-resistant housing containing a microprocessor, a sensor connected to the microprocessor and configured to sense a sterilization parameter regarding the sterilization of the component, and an electronic storage unit connected to the microprocessor and configured to record data from the sensor on the sterilization status of the component, wherein the electronic storage unit is configured to record start point, end point and intervening point data for the sterilization parameter during a sterilization event; and a medical device connectable to the component, the device including a central processing unit able to receive data stored on the tag regarding the sterilization status of the component.

2. The system of claim 1 wherein the tracking tag comprises a wireless network interface.

3. The system of claim 1 wherein the data on the sterilization status of the component comprises a time the component was last sterilized.

4. The system of claim 1 wherein the data on the sterilization status of the component comprises a time between sterilization cycles for the component.

5. The system of claim 1 wherein the data on the sterilization status of the component comprises an identifier of whether the component has not been subjected to proper sterilization.

6. The system of claim 1. wherein the data on the sterilization status of the component comprises a time for replacement of the component.

7. The system of claim 6 wherein the data on the time for replacement of the component includes a defined maximum number of autoclave cycles for the component and a number of actual autoclave cycles for the component recorded by the tag.

8. The system of claim 1 wherein the microprocessor is configured to receive data from the medical device for storage in the data record.

9. The system of claim 1 wherein the tag is adhesively secured to the component.

10. The system of claim 1 wherein the tag is directly formed as part of the component.

11. A tracking tag for a sterilizable medical device component, the tag comprising:
a sterilization-resistant housing;
a microprocessor;
at least one sensor connected to the microprocessor and configured to sense a sterilization parameter regarding the sterilization of the component;
an electronic storage unit connected to the microprocessor and configured to record data from the sensor on the sterilization status of the component, wherein the electronic storage unit is configured to record start point, end point and intervening point data for the sterilization parameter during a sterilization event, wherein the electronic storage unit also retains qualified sterilization parameter values for comparison by the microprocessor with the intervening point data for determining a sterilization status of the component; and
a wireless network interface operably connected to the microprocessor.

12. The tag of claim 11 further comprising a battery operably connected to the microprocessor.

13. The tag of claim 11 further comprising a wireless charging mechanism operably connected to the microprocessor.

14. A method of tracking the sterilization of a sterilizable component for a medical device, the method comprising the steps of:
providing a tracking tag including a sterilization-resistant housing containing a microprocessor, a sensor connected to the microprocessor and configured to sense a sterilization parameter regarding the sterilization of the component, and an electronic storage unit connected to the microprocessor and configured to record data from the sensor on the sterilization status of the component;
securing the tag to the component;
sterilizing the component and the tag; and
recording data concerning the sterilization event and status of the component within the tag
wherein the step of recording the data comprises:
sensing a sterilization event trigger;
recording start point, end point and intervening point data for the parameter during the sterilization event;
comparing the recorded intervening point sterilization event data to qualified parameter values for a validated sterilization event; and
storing the sterilization event data in a data record in the electronic storage unit.

15. The method of claim 14 further comprising the step of transmitting the data to a medical device utilized with the component for storage on the medical device.

16. The method of claim 14 further comprising the step of conducting and end of life determination on the component employing the sterilization event data.

17. The method of claim 14 further comprising the step of comparing the recorded sterilization event data to qualified entry and exit parameter values for a validated sterilization event.

18. The method of claim 17 further comprising the step of initiating an alarm on the medical device When the recorded sterilization event parameters do not meet the qualified entry and exit parameter values for a validated sterilization event.

19. The method of claim 14 further comprising the steps of:
connecting the sterilized component including the stored sterilization event data to the medical device for use with the device;
disconnecting the component from the medical device;
re-sterilizing the component and the tag; and
recording data concerning the re-sterilization event and status of the component within the tag.

* * * * *